US009090927B2

(12) United States Patent
Christensen et al.

(10) Patent No.: US 9,090,927 B2
(45) Date of Patent: Jul. 28, 2015

(54) METHOD AND APPARATUS FOR CONVERSION OF CELLULOSIC MATERIAL TO ETHANOL

(71) Applicant: Inbicon A/S, Fredericia (DK)

(72) Inventors: Borge Holm Christensen, Alsgarde (DK); Lena Holm Gerlach, Helsingor (DK)

(73) Assignee: Inbicon A/S, Fredericia (DK)

( * ) Notice: Subject to any disclaimer, the term of this patent is extended or adjusted under 35 U.S.C. 154(b) by 0 days.

(21) Appl. No.: 13/753,541

(22) Filed: Jan. 30, 2013

(65) Prior Publication Data

US 2013/0143263 A1    Jun. 6, 2013

Related U.S. Application Data

(62) Division of application No. 13/361,981, filed on Jan. 31, 2012, now Pat. No. 8,460,473, which is a division of application No. 11/989,027, filed as application No. PCT/DK2006/000419 on Jul. 19, 2006, now Pat. No. 8,123,864.

(60) Provisional application No. 60/700,323, filed on Jul. 19, 2005.

(30) Foreign Application Priority Data

Jul. 19, 2005    (EP) .................................... 05015641

(51) Int. Cl.
*C12P 7/06*    (2006.01)
*C12P 7/08*    (2006.01)
(Continued)

(52) U.S. Cl.
CPC ................ *C12P 21/00* (2013.01); *C08B 15/00* (2013.01); *C08B 37/0057* (2013.01); *C08H 6/00* (2013.01);
(Continued)

(58) Field of Classification Search
CPC ............... C12P 7/00; C12P 7/06; C12P 7/08; C08B 15/00; C08H 6/00; C08H 8/00; C10L 8/00; C10L 2290/00; C10G 1/008; C10G 1/00; C10G 2300/1011; C10G 2300/1014; B30B 13/00

USPC ......... 210/632, 634, 760, 766, 770, 774, 806, 210/808, 773; 127/34–37, 42, 43, 46.1, 53, 127/55, 65; 426/635, 636; 422/600, 608, 422/616, 618, 630, 638, 642, 646; 100/73–75, 35; 435/132–136, 435/161–165; 44/307, 450, 589, 590, 605, 44/606, 620; 585/240, 242
See application file for complete search history.

(56) References Cited

U.S. PATENT DOCUMENTS 3,972,775 A    8/1976    Wilke et al.
3,990,945 A    11/1976    Huff et al.
(Continued)

FOREIGN PATENT DOCUMENTS

EP    0187422 A    7/1986
FR    2332364 A    6/1977
(Continued)

OTHER PUBLICATIONS

Publication: Anne Belinda Bjerre et al, "Development of Chemical and Biological Processes for Production of Bioethanol: Optimization of the Wet Oxidation Proces and Characterization of Products", Riso National Laboratory, Roskilde, Demark, Feb. 1997.*
(Continued)

*Primary Examiner* — Joseph Drodge
(74) *Attorney, Agent, or Firm* — Alston & Bird LLP

(57) ABSTRACT

The present invention provides an apparatus and a method for conversion of cellulosic material, such as chopped straw and corn stover, and household waste, to ethanol and other products. The cellulosic material is subjected to continuous hydrothermal pre-treatment without addition of chemicals, and a liquid and a fiber fraction are produced. The fiber fraction is subjected to enzymatic liquefaction and saccharification. The method of the present invention comprises:
  performing the hydrothermal pre-treatment by subjecting the cellulosic material to at least one soaking operation, and conveying the cellulosic material through at least one pressurized reactor, and subjecting the cellulosic material to at least one pressing operation, creating a fiber fraction and a liquid fraction;
  selecting the temperature and residence time for the hydrothermal pretreatment, so that the fibrous structure of the feedstock is maintained and at least 80% of the lignin is maintained in the fiber fraction.

11 Claims, 3 Drawing Sheets

Figure 1:
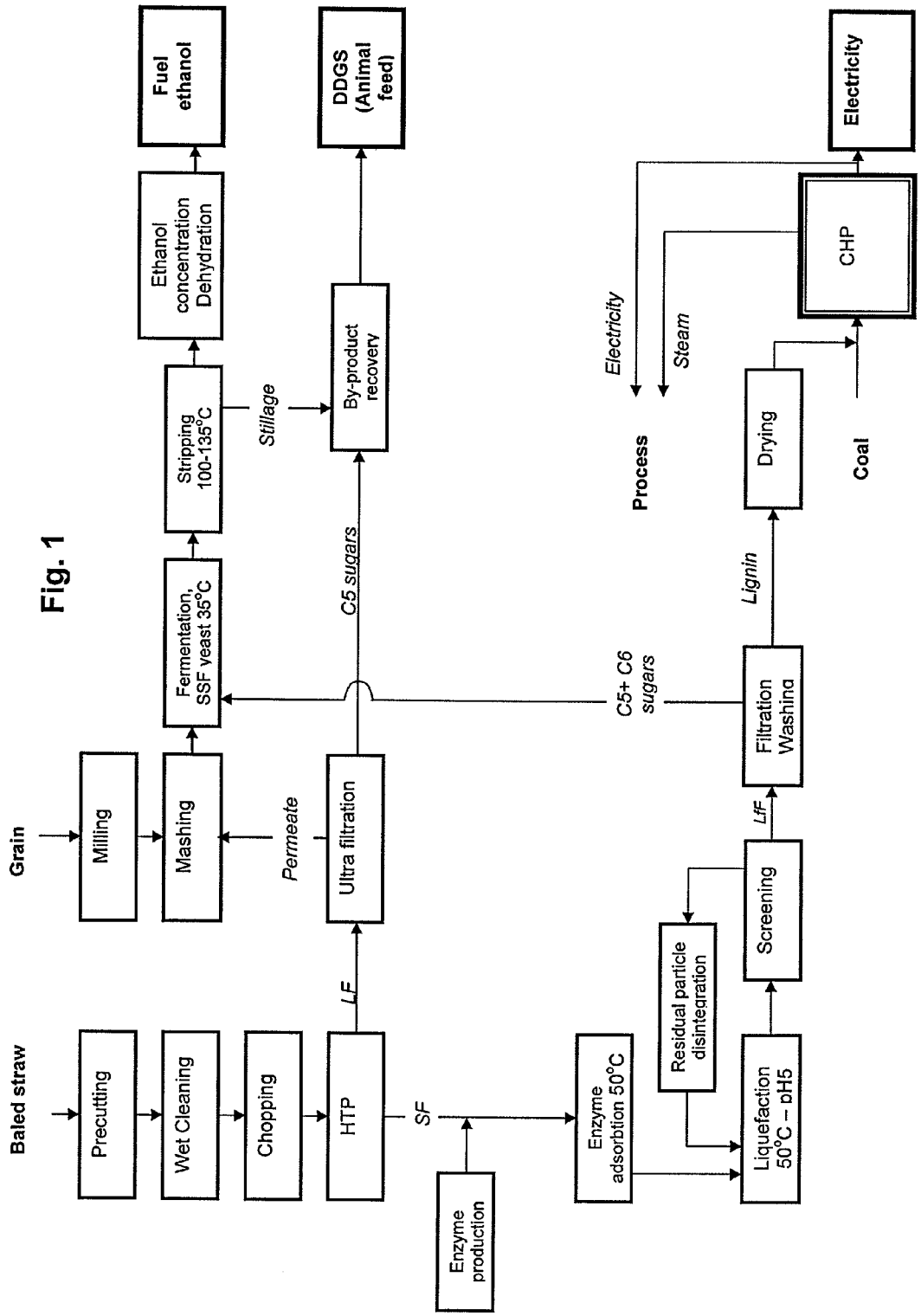

(51) Int. Cl.
| | |
|---|---|
| B30B 13/00 | (2006.01) |
| C10L 8/00 | (2006.01) |
| C10G 1/00 | (2006.01) |
| C12P 21/00 | (2006.01) |
| C08B 15/00 | (2006.01) |
| C08B 37/00 | (2006.01) |
| C08H 7/00 | (2011.01) |
| C08H 8/00 | (2010.01) |
| C12P 7/10 | (2006.01) |
| C13B 20/16 | (2011.01) |
| C13K 1/02 | (2006.01) |
| C12P 7/56 | (2006.01) |
| C12M 1/00 | (2006.01) |
| C12M 1/33 | (2006.01) |

(52) U.S. Cl.
CPC .............. *C08H 8/00* (2013.01); *C12M 21/12* (2013.01); *C12M 45/02* (2013.01); *C12M 45/04* (2013.01); *C12M 45/09* (2013.01); *C12M 45/20* (2013.01); *C12P 7/10* (2013.01); *C12P 7/56* (2013.01); *C13B 20/165* (2013.01); *C13K 1/02* (2013.01); *B01J 2219/00006* (2013.01); *C12P 2201/00* (2013.01); *Y02E 50/16* (2013.01)

(56) References Cited

U.S. PATENT DOCUMENTS

| | | | |
|---|---|---|---|
| 4,425,433 A | 1/1984 | Neves et al. | |
| 4,427,584 A | 1/1984 | LeGrand et al. | |
| 5,503,996 A | 4/1996 | Torget | |
| 5,693,296 A * | 12/1997 | Holtzapple et al. | 423/165 |
| 6,228,177 B1 * | 5/2001 | Torget | 127/37 |
| 6,419,788 B1 * | 7/2002 | Wingerson | 162/14 |
| 6,555,350 B2 * | 4/2003 | Ahring et al. | 435/161 |
| 7,504,245 B2 * | 3/2009 | Kinley et al. | 435/161 |
| 7,598,069 B2 * | 10/2009 | Felby et al. | 435/209 |
| 8,123,864 B2 * | 2/2012 | Christensen et al. | 127/37 |
| 8,460,473 B2 * | 6/2013 | Christensen et al. | 127/37 |
| 2005/0069998 A1 * | 3/2005 | Ballesteros Perdices et al. | 435/161 |
| 2005/0164355 A1 * | 7/2005 | Vlasenko et al. | 435/101 |
| 2006/0154352 A1 * | 7/2006 | Foody et al. | 435/161 |
| 2007/0175825 A1 * | 8/2007 | Denney | 210/631 |
| 2010/0041119 A1 | 2/2010 | Christensen et al. | |
| 2010/0255554 A1 | 10/2010 | Benson et al. | |
| 2012/0138246 A1 | 6/2012 | Christensen et al. | |

FOREIGN PATENT DOCUMENTS

| | | |
|---|---|---|
| FR | 2397486 A | 2/1979 |
| FR | 2509749 A | 1/1983 |
| FR | 2608625 A1 | 6/1988 |
| SU | 949002 B | 8/1982 |
| WO | WO 02/14598 A1 | 2/2002 |
| WO | WO 03/013714 A | 2/2003 |
| WO | WO 03/071025 A | 8/2003 |

OTHER PUBLICATIONS

Publication: Magnus Arnell, "Pretreatment of residual fibers from pulp and paper industry for anaerobic degeneration and biogas production", published by "vateknik.lth.se", 2005.*

Publication: Aners Thygesen et al, "Hydrothermal treatment of wheat straw on pilot plant scale", Published by The Royal Veterinary and Agricultural University, Tastrup, Denmark, 2004.*

International Application No. PCT/CA2010/000456, International Search Report dated Jul. 15, 2010.

Lu et al,. "Influence of High Solid Concentration on Enzymatic Hydrolysis and Fermentation of Steam-Exploded Corn Stover Biomass", Appl. Biochem Biotechnol., vol. 160, published online Jul. 15, 2008, pp. 360-369.

Rosgaard et al., "Effects of substrate loading on enzymatic hydrolysis and viscosity of pretreated barley straw", Appl. Biochem Biotechnol., vol. 143, published online Apr. 17, 2007, pp. 27-40.

Olofsson et al., "A short review on SSF—an interesting process option for ethanol production from lignocellulosic feedstocks", Biotechnology for Biofuels, vol. 1., No. 7, May 1, 2008, pp. 1-14.

Alvira et al., "Pretreatment technologies for an efficient bioethanol production process based on enzymatic hydrolysis: A review", Bioresource Technology, vol. 101, published online Dec. 29, 2009, pp. 4851-4861.

Andric et al., "Reactor design for minimizing product inhibition during enzymatic lignocellulose hydrolysis: I. Significance and mechanism of cellobiose and glucose inhibition on cellulolytic enzymes", Biotechnology Advances, vol. 28, Jan. 18, 2010, pp. 308-324.

Hodge et al., "Model-Based Fed-Batch for High-Solids Enzymatic Cellulose Hydrolysis", Appl. Biochem Biotechnol., vol. 152, published online Jan. 2009 pp. 88-107

International Search Report and Written Opinion for corresponding International Application No. PCT/DK2006/000419, mailed May 25, 2007.

PCT International Preliminary Report on Patentability for corresponding International Application No. PCT/DK2006/000419, mailed Jan. 16, 2008.

European Search Report on corresponding European Application No. 13174209 0, mailed Oct. 2, 2013.

Arnell, Magnus, "Pretreatment of residual fibers from pulp and paper industry for anaerobic degeneration and biogas production," published by "vateknik.lth.se", 2005.

Bjerre, A. B., et al., "Development of Chemical and Biological Processes for Production of Bioethenol: Optimization of the Wet Oxidation Process and Characterization of Products," *Riso National Laboratory*, Feb. 1997, Roskilde, Denmark.

Reith, H.J. et al., "Co-production of bioethanol, electricity and heat from biomass residues," presented on the 12th European Conference and Technology Exhibition on Biomass for Energy, Industry and Climate Protection, 2002.

Thygesen, A., et al., "Hydrothermal treatment of wheat straw on pilot plant scale," *The Royal Veterinary and Agricultural University*, Tastrup, Denmark.

* cited by examiner

METHOD AND APPARATUS FOR CONVERSION OF CELLULOSIC MATERIAL TO ETHANOL

This application is a divisional of U.S. application Ser. No. 13/361,981, which issued as U.S. Pat. No. 8,460,473, and which was a divisional of U.S. application Ser. No. 11/989,027, which issued as U.S. Pat. No. 8,123,864 and which was a national stage entry of PCT/DK2006/000419, international filing date 19 Jul. 2006, which claimed priority to EP 05015641.3, filed on 19 Jul. 2005, and to U.S. 60/700,323, filed on 19 Jul. 2005.

TECHNICAL FIELD

The present invention relates to sustainable methods for cost and energy effective conversion of lignocellulosic biomass to ethanol and other products based on continuous hydrothermal pre-treatment followed by enzymatic hydrolysis, ethanol fermentation and recovery.

BACKGROUND OF THE INVENTION

Lignocellulosic biomass contains variable amounts of cellulose, hemicellulose, lignin and small amounts of protein, pectin, wax, potassium chloride and other inorganic compounds. Lignocellulosic biomass should be understood in its broadest sense, so that it apart from wood, agricultural residues, energy crops also comprises different types of waste from both industry and households. Cellulosic biomass is a vast poorly exploited resource, and in some cases a waste problem. However, hexoses from cellulose can be converted by yeast to fuel ethanol for which there is a growing demand. Pentoses from hemicellulose can not yet be converted to ethanol commercially but several promising ethanologenic microorganisms with the capacity to convert pentoses and hexoses are under development.

The production cost of fuel ethanol from lignocellulosic feedstocks is at present much higher than from starch/sugar feedstocks.

Until recently, the cost of cellulytic enzymes for conversion of the pretreated cellulosic feedstock to fermentable sugars has been prohibitive.

This cost has been dramatically reduced caused by the successful research work carried out by Novozymes and Genencor, sponsored by Department of Energy, USA.

More cost reductions are however needed to establish a commercially viable exploitation of the huge quantities of lignocellulosic feedstocks.

PRIOR ART

Most of the prior art methods grind or mill the feedstock into a powder, which afterwards is mixed with water to form a slurry. This has some disadvantages:
  Large energy consumption for grinding or milling
  Large capital and operational costs for grinding or milling
  Large quantities of liquid are needed to suspend the particles into a pumpable slurry which can be processed
  It is difficult to remove the liquid again by mechanical dewatering Additionally, a large proportion of the prior art is only tested at laboratory scale, and fails to suggest solutions for up-scaling to industrial scale.

Conversion of cellulosic material to ethanol usually comprises a pre-treatment before the actual hydrolysis of the cellulose into fermentable sugars, in order to make the cellulose accessible to either enzymes or chemicals. The total impact from elevated temperatures, retention time, and chemicals are referred to as the severity of the process. This means, that the same results can be achieved with e.g. a shorter retention time, if the temperature is higher. In order to render the cellulose accessible for the cellulases, most of the pre-treatment methods of the prior art attempt to dissolve and remove as much of the hemicellulose and lignin as possible, in order to create larger "pores" and allow greater contact between cellulose and cellulase. The problems associated with inhibitors produced by this type of pre-treatment are solved in different ways, such as by introduction of a detoxification step, or by removal of the dissolved components as soon as possible.

In "The Alcohol Textbook" third edition 1999, chapter 9, J. S. Tolan offers an overview of the production process of fuel ethanol from cellulosic biomass implemented at Iogen's pilot plant.

Tolan underlines that a preatreatment process is necessary in order to make the cellulose accessible to enzymes and compares 3 options:
  Solvent based pre-treatment, where organic solvents dissolve the lignin. However lignin is not considered a significant barrier to cellulose.
  Alkali pre-treatment, which will not form furfural, but destruction of the hemicellulose has been reported
  Dilute acid pre-treatment is preferred by Iogen, because it is mild to hemicellulose and produces a material with a high surface area. By this method, the lignin is depolymerised, but not dissolved, and the low levels of acid preclude the need for recovery. As a result of Iogen's pre-treatment, the fibrous structure of the feedstock is destroyed, and it gets a muddy texture and a dark brown colour.

Cellulases are primarily made from the fungus Trichoderma in submerged liquid culture in fermentation vessels. Production of enzymes at the ethanol plant has the advantages that purification, concentration and storage can be omitted, and some of the hydrolysis sugar can be used for the enzyme production.

Following Iogen's pre-treatment, the feedstock is conveyed to the hydrolysis tank as a slurry with 15-20% solids, or as much as can be handled. The agitation in the tank is more gentle than that normally used in a fermentation tank, but has to be sufficient to keep solids dispersed and move the material. The hydrolysis lasts for 5-7 days. The viscosity decreases, and the lignocellulosic particles become smaller. Approximately 80-95% of the cellulose will be converted, while the rest is inaccessible to the enzymes because it is covered with lignin.

By enzymatic conversion of cellulose to glucose, product inhibition from cellobiose and glucose is a problem. It has often been suggested to conduct a simultaneous saccharification and fermentation (SSF) process, in order to overcome product inhibition from glucose on β-glucosidase. However the simultaneous saccharification and fermentation (SSF) process has non-optimal operation conditions, because the optimum temperatures for the enzymes (50° C.) and the yeast (28° C.) are too wide apart, and the medium temperature (37° C.) has a high risk for microbial contamination. Another possibility is to produce β-glucosidase separately, which confers additional costs for a further fermentation process. Iogen has chosen to develop Trichoderma strains, which produces more β-glucosidase.

Tolan describes a dramatically declining conversion rate. After 24 hours it is less than 2% of the initial rate. The reasons for this decline are not fully understood.

Tolan lists several possibilities to improve enzyme efficiency:

More enzyme, shorter time, which, however, by the present inventors and Tolan is seen as being disadvantageous from an economical perspective.

Recycle of enzyme, which however requires more research.

Continuous or fed batch systems. This might allow for high cellulose concentration at all times.

Better cellulase enzymes. Much research was already done, but the approach can be developed further with new techniques in molecular biology New reactors. Much research was already done, however a better understanding of how the enzymes function would be helpful in evaluating new reactors.

Better pre-treatment. This approach has been widely studied, however it may still be possible to improve.

After hydrolysis, the insoluble material, mainly lignin and residual cellulose, are separated from the liquid fraction by plate and frame filter, washed 2-3 times with water to obtain high sugar recovery. The liquid fraction is pumped to the fermentation tanks, the solid fraction is spray-dried and combusted to generate power for the plant.

Tolan refers to the on-going work of finding microorganisms, which can ferment C5 sugars to ethanol, which at that time still was not successful.

NREL report 99-10600/18 "Acid hydrolysis reactors, Batch system" "Process design and cost estimate of critical equipment in the biomass to ethanol process" describes that corrosion of the equipment is a severe problem, under acidic conditions and high temperatures (high severity). By batch processes it is a further problem for the equipment, that the temperature is alternating between the maximum processing temperature and the loading temperature.

U.S. Pat. No. 5,503,996 (Torget) discloses a prehydrolysis of lignocellulose, in which an acidic solution is passed through lignocellulosic particles with removal of soluble components as they are formed using a flow-through system where fluid moves with respect to the solid lignocellulose. During prehydrolysis, the hot biomass is separated in a solid fraction and a hydrolysate, of which the latter contains more than 90% of hemicellulose sugars, up to 25% of the cellulose sugars and 20-50% of the Klason lignin. The method of U.S. Pat. No. 5,503,996 achieves this degree of hydrolysation with a relatively small amount of added acid.

U.S. Pat. No. 6,228,177 (Torget) discloses a hot wash process after the pre-treatment, in order to prevent the lignin from recondensing/reprecipitate on the cellulose. The hot wash is carried out at about 140° C., which is a significantly lower temperature than the temperature of the pre-treatment. Acid is either added during the pre-treatment or during the hot wash. Improved cellulase digestibility has been measured after the hot wash. By combining the two processes disclosed by Torget, a substantial part of the lignin (20-50%) is solubilized of which the major part is washed out together with the hemicellulose by the hot wash. The wash water with the mixture of hemicellulose sugars and solubilized lignin is however very difficult to convert economically into marketable products.

Enerkem Technologies, Canada, have developed the "FIRST" pre-treatment method, wherein the feedstock is impregnated with acid followed by rapid steam treatment. This method has the advantage, that it can operate with high dry matter to liquid ratio. The use of acid leads to different problems such as formation of inhibitors and extra cost connected to the recovery and handling of the acid.

U.S. Pat. No. 6,555,350 B2 (Birgitte Ahring and Anne Belinda Thomsen) discloses a pre-treatment method based on alkaline wet oxidation or steam explosion where the effluent from the ethanol fermentation is treated with microorganisms to generate biogas and to reduce the content of inhibitory substances in the water effluent to a level which permits a larger part of it to be recycled into the process, than by a process without the biogas.

US 2005/0069998 (Ballesteros) describes a pre-treatment method without the use of acid or other chemicals. The method is based on steam explosion followed by separation in a liquid and solid fractions. The solid fraction is subject to simultaneous saccharification and fermentation (SSF), using a heat resistant yeast strain in order to overcome the problem of different optimum temperatures described by Tolan. It is described, that the method is discontinuous, and that the reactor is opened and closed by hand. There is no indication of how to upscale the method to an industrial production method.

The energy consumption for production of ethanol from grain is relatively high because of the great steam demand for distillation, evaporation, heating etc. The total consumption per kg ethanol in modern operations amount to about 3.25 Mcal steam and 0.33 Mcal or 0.38 KWh electricity corresponding to about 50% of the gross heating value of ethanol (7 Mcal/kg). To cover this demand, most ethanol plants have steam generation facilities but obtain electricity from the grid. Some ethanol plants have a combined heat and power plant (CHP) with the capacity to produce all the steam and electricity required by the production process, but are connected to the grid, which allow them to obtain and deliver moderate amounts of electricity.

The energy consumption for production of ethanol from lignocellulosic feedstocks such as cereal straw and corn stover using the methods described in the prior art is much higher in terms of both steam and electricity than in respect of starch/sugar based production. Integration with a combined heat and power plant (CHP) is therefore of great interest.

A review of the state of the art in this field is offered in the paper "Co-production of bio-ethanol, electricity and heat from biomass residues" J. H. Reith et al, presented on the 12th European Conference and Technology Exhibition on Biomass for Energy, Industry and Climate protection, 2002.

This paper compares the existing production of ethanol based on starch/sugar crops with the cellulose-to-ethanol production under development.

The paper proposes a thermal conversion of the substantial amount of non-fermentable residues in an integrated gasifier and combined cycle system to provide the total steam and electricity requirement for the production process and an electricity surplus for export to the grid, resulting in a total system energy efficiency of 56-68%.

The paper underlines that no suitable fermentation system is available for the fermentation of pentoses from the hemicellulose fraction, that at least a 10 fold increase of cellulase cost-effectiveness is required, that the water consumption is 3-5 times higher than by ethanol production from starch/sugar, and that capital costs need to be reduced by 30%

In order to reach ethanol production costs competitive with ethanol from sugar/starch crops.

NREL report "Bioethanol Co-location study" concludes that there are large advantages by co-location of a cellulosic material ethanol plant with a combined heat and power (CHP) plant, and that the advantages are even larger by co-location with a CHP that is fired with fossil fuel. Some of the main advantages are:

reduced capital costs,
easy access to low cost steam and electricity,
equipment to combust the lignin/cellulose residue,
reduced operating costs,
safe fuel supply,
Access to established transmission and distribution network for bioelectricity.

The report underlines that handling and co-firing of lignin is likely to lead to technical problems, because lignin is a material very different from coal.

Another problem underlined in the report is the difficulty to achieve economy of scale with lignocellulosic residues alone, since long transportation is environmentally and economically prohibitive. The report suggests that methods are developed, to use a mixture of lignocellulosic residues and starch/sugar feedstocks or lignocellulosic energy crops in order to achieve economy of scale.

DESCRIPTION OF THE INVENTION

In a first aspect, the present invention provides an apparatus and a method for conversion of cellulosic material, such as chopped straw and corn stover, chopped whole cereal and corn crops, bagasse wood chips and household waste, to ethanol and other products, the cellulosic material comprising primarily cellulose, lignin, hemicellulose and ash. In the method of the first aspect of the present invention, the cellulosic material (also referred to as raw material) is cleaned and subjected to continuous hydrothermal pre-treatment without addition of acids or bases or other chemicals, which must be recovered, and a liquid and a fibre fraction are produced. While different options exist for utilisation of the liquid fraction, the fibre fraction is subjected to enzymatic liquefaction and saccharification. The method further includes ethanol fermentation and product recovery. The method of the first aspect of the present invention comprises:

performing the hydrothermal pre-treatment by subjecting the cellulosic material to at least one soaking operation, and conveying the cellulosic material through at least one pressurised reactor defining a reactor pressure zone at an elevated pressure; the cellulosic material being heated to a temperature between 170 and 230° C., and subjecting the cellulosic material to at least one pressing operation, creating a fibre fraction and a liquid fraction;

selecting the temperature and residence time for the hydrothermal pretreatment, so that the fibrous structure of the feedstock is maintained and at least 80% of the lignin is maintained in the fibre fraction;

unloading the pressed fibre fraction from the reactor pressure zone to a downstream closed zone, which is at a lower pressure than the reactor pressure zone, while collecting the released steam without access for air;

unloading the liquid fraction from the pressurised reactor to a second closed zone, which is at a lower pressure than the reactor pressure zone, while collecting released steam without access for air.

The first aspect of the invention also provides an apparatus for conversion of cellulosic material to ethanol and other products, the cellulosic material comprising at least cellulose, lignin, hemicellulose and ash, the apparatus comprising a cleaning device for cleaning the cellulosic material, a hydrothermal pre-treatment device for subjecting the cellulosic material to continuous hydrothermal pre-treatment without addition of acids or bases or other chemicals, which must be recovered, the apparatus being suitable for producing a liquid and a fibre fraction, the apparatus further including structure for subjecting the fibre fraction to enzymatic liquefaction and saccharification, and structure for ethanol fermentation and product recovery, wherein the hydrothermal pre-treatment device is arranged to perform the hydrothermal pre-treatment by subjecting the cellulosic material to at least one soaking operation; the apparatus comprising:

at least one pressurized reactor, through which the cellulosic material may be conveyed, the at least one pressurized reactor defining a reactor pressure zone operable at an elevated pressure; the pressurized reactor being arranged to heat the cellulosic material to a temperature between 170 and 230° C., the pressurized reactor further including a pressing device for pressing the cellulosic material to thereby create a fibre fraction and a liquid fraction, whereby the hydrothermal pre-treatment device is adapted to maintain such temperatures and residence times for the hydrothermal pretreatment that the fibrous structure of the feedstock is maintained and at least 80% of the lignin is maintained in the fibre fraction;

a fibre fraction unloading mechanism for unloading the pressed fibre fraction from the reactor pressure zone to a downstream closed zone, which is at a lower pressure than the reactor pressure zone, while collecting the released steam without access for air;

a liquid fraction unloading mechanism for unloading the liquid fraction from the pressurised reactor to a second closed zone, which is at a lower pressure than the reactor pressure zone, while collecting released steam without access for air.

In embodiments of the invention, the pressurised reactor may constitute or be comprised in the hydrothermal pre-treatment device.

The method and apparatus of the present invention may also provide for optional integration with ethanol production from sugar/starch feedstocks and optional integration with a combined heat and power (CHP) plant.

It is a goal of preferred embodiments of the invention to improve the economical and environmental viability of conversion of cellulosic material to ethanol. In order to achieve this it is desirable that:

the method, besides ethanol, provides a residual organic product with a low content of KCl, which can be converted to more energy than the demand for the process.

The method may utilize various types of feedstock, so that the most profitable feedstocks can be used.

All of the components of the cellulosic material are converted to marketable products.

The process is continuous.

All process steps can work with high concentration of dry matter.

There is no waste water.

The usage of make-up water is very low.

That the production is safe and reliable

There is no risk of air pollution.

That the ethanol production is sustainable

In preferred embodiments of the invention, some measures to achieve these goals are:

Applying a soaking—pressing based hydrothermal pre-treatment process at low severity, allowing at least 80% of the lignin content of the cellulosic material to be maintained in the fibre fraction in solid form.

Collecting the steam released from the hydrothermal pre-treatment process and reuse it in evaporation processes.

Utilisation of condensate from evaporation processes as make-up water.

Utilisation of all liquid non-fermentables as feed or fertilizer.

Utilisation of solid non-fermentables as a solid biofuel for generation of more energy than used in the process.

Instead of relying on a flow through system, where a liquid must move in respect to the solids, the method of the invention preferably utilises a soaking-pressing system.

In this context, soaking implies that there is sufficient fluid present that a substantial part of it can be removed by the chosen pressing device. Pressing implies that a substantial part of the liquid is removed again by mechanical means.

The soaking-pressing operations require that the fibrous structure of the feedstock is maintained. Therefore it is preferred that the method is carried out with a high content of rather large particles.

By using soaking-pressing operations:
The need for energy demanding and expensive milling and grinding may be eliminated or at least reduced.
The water to cellulosic material dry matter ratio can be reduced to 6:1 or even lower.
A reliable contact between solids and liquid can be secured with a higher concentration of solids dry matter in the reactor, than by a flow trough system.
The equipment is able to handle large objects, such a books and large lumps of wasted food from household waste, and make it ready for the liquefaction process. Even nonfermentable objects such as pieces of plastic can pass the hydrothermal pre-treatment and be sorted out after liquefaction.

Opposite most of the prior art, it is not a goal of the method according to the invention to remove as much hemicelluloses and lignin from the fibre fraction as possible during the pre-treatment. While applicants do not wish to be bound by any particular theory, they believe that when lignin is melted in the presence of water, the hydrophobic lignin will form micro-droplets which will solidify at lower temperatures and form micro-particles without any or very little cellulose protective effect. When hemicellulose and lignin do not have to be removed from the fibre fraction, the pre-treatment can take place at a lower severity.

Operating at low severity conditions has the following advantages:
Acids and bases, which have to be recovered can be omitted, this saves substantial capital and operational costs, since equipment for recovery can be saved, and problems with corrosion are substantially reduced
the fibrous structure of the feedstock can be maintained
the formation of inhibitors is reduced
very little lignin is dissolved Certain steps of preferred embodiments of the invention will now be described further:

Cleaning of the Raw Material

Since the cellulosic material often contains impurities like stone, sand and other undesired objects, it is an advantage to clean it to some degree. In respect of some types of dry feedstock such as straw, dust constitutes a problem, since it leads to poor working environment, risk for fires and dust explosions. A wet stonetrap will, at the same time clean the cellulosic material from stones, sand and other heavy items, and wet the cellulosic material, which will solve the dust problems. If the cellulosic material has to be chopped, it is an advantage to chop it after it has been wetted in the stonetrap, since most cellulosic materials are easier to chop when they are wet. The wet stonetrap can be combined with the pre-soaking step explained later, so that the pre-soaking reactor also works as a stonetrap.

Hydrothermal Soaking—Pressing Pre-Treatment

The hydrothermal pre-treatment is performed as an extraction with hot water, thereby producing a fibre fraction containing the major part of the cellulose, more than 80% of said lignin comprised in the cellulosic material, and a liquid fraction containing some C5 sugars from the hemicellulose, a majority of said alkali chlorides comprised in the cellulosic material and a majority of fermentation inhibitors (mainly acetic acid) produced by the hydrothermal pre-treatment.

The cellulosic material is conveyed through at least one pressurised reactor, defining a reactor pressure zone at an elevated pressure, the cellulosic material being heated to a temperature between 170 and 230° C. for effecting the hydrothermal pre-treatment. The temperature may be between 180 and 210° C., such as between 190 and 200° C.

Unloading the fibre fraction from the reactor pressure zone to a downstream pressure zone, which is at a lower pressure than the reactor pressure zone, while collecting released steam without access for air. A preferred dry matter content is between 20-60% and more preferred 30-50% and most preferred 35-45%.

Unloading the liquid fraction from the pressurised reactor to a upstream pressure zone, which is at a lower pressure than the reactor pressure zone, while collecting released steam without access for air.

One first step of the hydrothermal pre-treatment may comprise soaking under ambient pressure and at temperatures up to 100° C., which may take place in the acetic acid containing liquid fraction from a subsequent step. The objective of the soaking is to drive out air from the feedstock and to ensure that all of the feedstock is saturated with the liquid. A further objective is to utilise some of the energy of the liquid fraction to increase the temperature of the feedstock. Further objectives of the soaking step are to increase the dry matter content in the liquid fraction and to impregnate the feedstock with the organic acids generated by subsequent steps.

Before or during transfer to the next step, the cellulosic material may be subjected to a pressing operation. The objectives of the pressing operation are to increase the solids concentration, to avoid heating of unnecessary liquid, and to transfer dissolved material to the liquid fraction.

The next step may be a pressurized treatment at temperatures between 170° C. and about 230° C., carried out e.g. as a high-solids plug flow process. The high temperature is achieved by adding hot water or steam. If steam is added, a part of it will condense on the colder cellulosic material. The addition of water or steam lets this process step have the function of a second soaking operation.

In order to achieve the desired economical benefit, at least the pressurised part of the hydrothermal pre-treatment should preferably take place with a high concentration of solids dry matter in the reactor. Thus, the reactor is preferably 100% filled, and for voluminous feedstocks compaction is an envisaged option. Continuous reactors with high solids dry matter content, based on a screw device, are often a cost effective solution, but in case of 100% filling, the transport function of the screw device may be insufficient. Embodiments of the reactor may thus include an intermeshing twin screw device or a single screw device with reciprocating axial movement. By an industrial scale production, these reactors, and the screw devices will be so large, that they can easily handle large objects.

The pre-treatment is based on treatment with water without addition of acids, bases or other chemicals which have to be recovered. This means that less dry matter is transferred from the feedstock to the liquid fraction (the extract) than by most other pre-treatment processes.

The transfer of lignin will normally be less than 20% of the original content of the feedstock. A substantial part of the hemicellulose will normally be hydrolysed but mostly to oligomers and soluble polymers, of which only a minor part will be transferred to the liquid fraction.

Omitting addition of acids lets the cellulosic material maintain the fibrous structure, which is desirable in order to conduct said pressing operations, and it means low formation of fermentation inhibitors. Furthermore, the small amounts of inhibitors (mainly acetic acid) will be concentrated in the liquid fraction of the pre-treatment where a detoxification, if needed, can be conducted at low cost. If needed, detoxification with $NH_3$ is preferred for the method according to the invention The solids dry matter concentration during soaking will typically be 10-20%, and after pressing 30-40% such that approximately 2.5-3.5 kg liquid per kg solids dry matter is added during soaking and removed again during pressing.

Each soaking and pressing step will transfer dry matter from the solids to the liquid fraction.

The main objective of the hydrothermal pre-treatment of the invention is to make the cellulose accessible for enzymatic hydrolysis/attack. In opposition to, e.g., the method of Torget, it is not a particular objective to remove the hemicellulose and lignin from the fibre fraction, but to neutralize their protection of the cellulose. While applicants do not wish to be bound by any particular theory, they believe that when lignin is melted in the presence of water, the hydrophobic lignin will form micro-droplets which will solidify at lower temperatures and form micro-particles without any or very little cellulose protective effect. The lignin melting conditions of the hydrothermal pre-treatment will hydrolyse the hemicellulose to a degree, where it will no longer protect the cellulose against enzymatic attack. It is also believed that the lignin melting conditions will eliminate crystallinity of the cellulose which is beneficial to achieve efficient enzymatic hydrolysis, however the fibrous structure of the cellulosic material is maintained. In order to improve the release of the melted lignin from the cellulose fibres, the feedstock is subjected to shearing forces. This will rub the lignin from the cellulose and facilitate the formation of free hydrophobic lignin droplets. The droplets seem to be coated by hydrophilic compounds mainly deriving from the partly hydrolysed hemicellulose. The resulting lignin microparticles have surprisingly very little or no inhibiting effect on the enzymatic hydrolysis and ethanol fermentation based on yeast. The main advantages of this approach are:

The hydrothermal pre-treatment of the invention can be carried out at less severe conditions, which as described earlier reduces capital and operational costs The separation of the pretreated cellulosic material in a fibre fraction and a liquid fraction is facilitaded The shearing forces can be applied by different means e.g. by the transportation device in the reactor, by devices moved by the transportation device or by pressing during loading and unloading of the reactor. Shearing forces can also be applied by steam explosion, applied during unloading, which primarily have the effect of blowing up the cells and capillaries. The means for applying shearing forces can be applied alone or as a combination of more than one means.

It is an interesting effect of the present invention that chopped straw subjected to the hydrothermal pre-treatment has a much higher feeding value than the untreated straw, because of the improved access for digestive enzymes.

One of the problems of industrial scale continuous, pre-treatment of voluminous feedstocks with high concentration of long particles, such as cereal straw or corn stover, is to transfer the feedstock into the pressurized reactor in a safe, efficient and reliable way. It is an advantage to load feedstocks into the reactor in portions with a sluice type loading device such as the particle pump described in WO 03/013714A1, wherein at any time at least one pressure lock secures pressure tight sealing between the pressurized reactor and the soaking vessel. This particle pump can remove liquid from soaked feedstock by pressing during loading and unloading of the reactor, and unloading can be combined with steam explosion.

Also household waste from which the large or heavy components have been removed in an upstream separation process, but which still comprise remaining large particles such as cans, plastic bottles, pieces of plastic and wood can be loaded and unloaded by the said particle pump, and processed in the pre-treatment and liquefaction reactors. The non-liquefied particles can be removed before or after fermentation. This is possible because all preferred process equipment of the invention can accept relatively large particles.

According to an embodiment of the present invention, the pressurized part of the hydrothermal pre-treatment can be conducted at one or more sets of temperature/pressure conditions. Transfer of the feedstock from one pressure zone to another will normally be conducted by a sluice system with a pressing device such as the particle pump described in WO 03/013714A1. Additional pressing/soaking operations can be conducted within each pressure zone.

According to an embodiment of the invention, when the hydrothermal pre-treatment is carried out in several sets of temperature/pressure conditions, the temperature/pressure will increase for each step. Since it is a counter current process with pressing between each set of temperature/pressure conditions, the chemical severity will drop as the thermal severity rises, which is important to avoid corrosion problems of the equipment. Since acids are formed during the hydrothermal pre-treatment, this also has the advantage that the pH will be relatively close to neutral in the fibre fraction, because the liquid added to the last step is not acidic. This means that the pH will be close to the optimum for the enzymatic liquefaction, and only limited adjustment is required. The removal of acid from the fibre fraction is also an advantage when the feedstock is silage, because the high content of lactic acid will be washed out already during the pre-soaking.

The pretreated feedstock can either be pressed, while it is still under high temperature conditions with lignin in the form of micro-droplets, or it can be pressed after it has been unloaded from the hydrothermal pre-treatment reactor with lignin in the form of solid micro-particles.

One advantage of pressing before the feedstock is unloaded is that a higher dry matter content in the fibre fraction can be achieved. Another advantage by pressing under hot pressurized conditions is that the shearing forces generated during pressing will provide improved release of lignin droplets and disintegration of lignocellulosic particles. The advantage of pressing at temperatures below 100° C. is that the cost is lower and that more lignin will remain in the fibre fraction.

The depressurization of both the solid and the liquid fraction may be carried out in closed systems without access of air, in order to collect the released steam and to use the thermal energy of the steam for concentration purposes and the condensate as process water.

The unloading of the fibre fraction can also be carried out by a pressing device, e.g. a screw press, since the high pressure will fill channels with material, so that leakage is avoided. This type of unloading will preferably be carried out with a first step, where the pressure lock between the pressurized reactor and a downstream closed compartment with a lower pressure is provided by a screw press, conducting the pressing operation at the outlet of the pressurised reactor, the resulting liquid is sent upstream and the resulting solids are the fibre fraction going downstream. The pressure of said closed compartment is preferable 2-6 bar. By the second step, the fibre fraction is conveyed downstream to a second closed compartment with a pressure of 1 bar or lower by a second screw press providing the pressure lock between the two compartments. Process water at a temperature lower than that of the fibre fraction is injected into the second screw press at the first part of the screw, reducing the temperature of the fibre fraction to 100° C. or lower.

In order to achieve an efficient enzymatic liquefaction, it is desirable that as many enzymes as possible are placed on the surfaces of the accessible cellulose fibres contained in the particles of the pretreated fibre fraction. To achieve this, the relatively warm pressed fibre fraction is mixed with a relatively cold enzyme preparation which may be sucked into the cavities of the particles. The steam trapped in the cavities condenses as it is cooled by the enzyme preparation and creates a vacuum pulling the enzyme preparation into the cavities. By adjusting the concentration of enzymes in the preparation, the desired amount of enzymes can be placed at the inner and outer surfaces of the particles, adhering to the cellulose fibres. By virtue of this adhesion, the dry matter content of the enzyme-loaded fibre fraction can be increased by pressing, while preventing removal of enzymes to an unacceptable extent.

By adjusting the temperature and pH of the enzyme preparation before mixing with the warmer pretreated SF, liquefaction conditions can be improved.

As described by Tolan, enzyme preparations for hydrolysis of cellulose will normally contain three types of enzymes: endogluconase, cellobiohydrolase and beta-glucosidase. The first two hydrolyse the polymer cellulose to its soluble dimer cellobiose which is then hydrolysed to glucose by the third type. Product inhibition from cellobiose and glucose can be prevented or reduced by increasing the concentration of beta-glucosidase and use separate hydrolysation and fermentation. Another solution is to use the simultaneous saccharification and fermentation (SSF) process, wherein the cellobiose and the glucose are converted to ethanol by the fermenting organism. One embodiment of the present invention is based on a successful development of thermophilic ethanologenic microorganisms with the capacity to ferment both C5 and C6 sugars and compatible enzyme systems with high hemicellulase and cellulase activity at temperatures around 60° C. and at pH around 6. Of special interest for the present invention is thermophiles with the capacity to ferment not only monomers but also small oligomers such as cellobiose, maltose and raffinose simultaneously, which together with a compatible enzyme system will create a simultaneous saccharification and fermentation process (SSF) to convert the pretreated biomass of the invention to ethanol. As an alternative, the method according to the invention may use an approach, in which a separate liquefaction step is introduced, providing optimal conditions for the activity of the enzymes followed by simultaneous saccharification and fermentation process (SSF) with the liquefied fraction as substrate and with optimal conditions for the fermentation organism, but suboptimal conditions for the enzymes.

During the liquefaction step catalysed for example by Tricoderma cellulases at pH around 5 and temperature around 50° C. the endogluconases may provide most of the depolymerisation because the activity of the cellobiohydrolases is swiftly inhibited by accumulated cellobiose and the beta-glucosidase is inhibited by accumulated glucose.

The liquefaction can be conducted by two principles, liquid or solid state liquefaction.

By solid state liquefaction, the enzyme-loaded fibre fraction is transferred into a mixer, which does not contain free liquid in the inlet area.

At solid state liquefaction on industrial scale, the microscopic movement of the enzymes from attack to attack on the cellulose may not always be provided by conventional stirring, because of the great power input required to overcome friction between the particles. Instead, technology used in the composting industry can be applied, such as composting drums, where the fibre fraction loaded with enzymes is subjected to a number of lifts and falls during the transport through the cylindrical drum, which is rotating or stationary and equipped with a rotor with lifting devices. After few hours, the liquid produced will make it possible to finalize the process as liquid state liquefaction.

By liquid state liquefaction, the incoming enzyme loaded particles of the fibre fraction is submerged into the viscous fluid of liquefied material. Even though the mixture may be highly viscous, the mixing can be carried out by a variety of known mixing devices.

Some advantages of liquid state liquefaction are:
  dry matter loading of the reactor can be high,
  transmission of suitable forces to ensure that the enzymes move from attack to attack on the cellulose fibres is facilitated by the liquid,
  recycling of liquefied fraction with free enzymes to the inlet region is possible, which will create good conditions for active enzymes to adhere and attack fresh cellulose fibres.

The liquid state liquefaction reactor according to the present invention can be based on an elongated horizontal cylindrical container with an inlet for the enzyme-loaded fibre fraction at a top section of one end of the container and an outlet for the liquefied fraction at a bottom section of the other end of the container.

At the inlet, a perforated device may force the particles of the fibre fraction towards the outlet, completely submerged in the liquefied fraction. At the outlet, a screening device may separate the residual macroparticles, consisting mainly of cellulose and lignin, from the liquefied fraction consisting mainly of a solution of liquefied polysaccharides and suspended lignin microparticles. During the passage through the reactor, the structure of most of the lignocellulosic particles will gradually disappear, while residual macroparticles may be sorted out, disintegrated and recycled to the inlet of the reactor. Alternatively, the residual macroparticles can be added to a solid biofuel product.

Both the solid state and the liquid state liquefaction are unsensitive to large objects.

The micro-particles of lignin can be removed either after the separate liquefaction process or after the fermentation process by known means such as pressure or vacuum filtration providing a filter cake with a high dry matter content, whereby low drying costs are achieved. This product usually has a low content of KCl and can therefore be combusted in combined heat and power plants with high electricity efficiency. The filtrate may be pumped to a feed tank, where temperature, pH and the content of nutrients may be adjusted to optimize the conditions of the subsequent simultaneous saccharification and fermentation process (SSF). If the simultaneous saccharification and fermentation process (SSF) is based on yeast, the temperature should be lowered to about 35° C. whereas the pH 5 can be maintained.

If the simultaneous saccharification and fermentation process (SSF) process is based on a C6 and C5 fermenting thermophile microorganism, such as TMO Biotec's thermophiles, the temperature may have to be increased to about 60° C. and the pH to about 6.

The simultaneous saccharification and fermentation process (SSF) disclosed herein can be carried out as a fed batch or a continuous process relying on equipment known per se, as described in "The alcohol textbook $3^{rd}$ Edition 1999 Nottingham University Press.

Recovery of ethanol can be carried out by conventional distillation technology.

A preferred recovery technology for the present invention is to use a stripping technology, such as vacuum stripping, gas stripping or spray evaporation, by which the temperature of the broth can be kept close to the fermentation temperature during removal of the ethanol. Thereby, thermal inactivation of enzymes and fermenting organisms is limited, and the enzymes and fermenting organisms can therefore be recycled and provide further cost reductions.

The lignin microparticles can be kept in the liquefied fraction during fermentation because no or very little inhibitory effect is associated with the microparticles of macromolecular lignin. Simultaneous ethanol fermentation and recovery is an interesting cost reducing option for the method according to the invention wherein the ethanol will be removed before inhibition starts to slow down the rate of saccharification or fermentation.

The use of the liquid fraction from the hydrothermal pretreatment, depends on many factors, e.g. whether the process is integrated with ethanol production from sugar/starch feedstock, and whether competitive organisms for C5 fermentation are available. A preferred option of the invention is to neutralize the content of acetic acid with $NH_3$, and combine it with the thin stillage from the fibre fraction conversion, and concentrate mixture and use the syrup in ruminant feed, since ruminants can easily digest C5 sugars. This option has the advantage, that N, P, K and other plant nutrients can be led back to the fields. If a suitable microorgansim for conversion of C5 sugars to ethanol is developed, the mixture can be used as fermentation feedstock. It can also be used as feedstock for production of single cell protein, lactic acid and enzymes.

The integration of ethanol production from lignocellulosic feedstocks with ethanol production from starch/sugar feedstocks is an advantageous option for the method of the invention because it can provide substantial reductions both in capital cost and cost of operation, especially in cases where it is difficult to collect enough lignocellulosic feedstock to produce about 100 000 t/y or more of fuel ethanol which is needed to take full advantage of the economy of scale. Furthermore, cost reductions can be achieved by using at least a part or a fraction of the liquid fraction from the pre-treatment to replace the water or part of it required in the mashing of starch/sugar feedstocks with high dry matter content. This is possible if the liquid fraction produced according to the invented method has a low or no content of inhibitors, which is usually the case. A significant part of the hemicellulose dissolved in the liquid fraction will be oligomers, and it is therefore possible to separate the liquid fraction into two fractions by ultra filtration. One fraction contains mainly pentose oligomers and has a high dry matter content, and the other fraction (the permeate) with low dry matter content contains mainly alkali chlorides and small organic molecules. This fraction is particularly suited for replacing make-up water in the grain mashing process. The oligomeric pentose fraction can be used as fermentation feedstock for ethanol production when relevant C5 sugar fermenting microorganisms are available. In the meantime it can be further concentrated and sold as feed for ruminants. Microorganisms in the ruminant can convert the pentose oligomers to short-chain fatty acids.

When the sugar/starch feedstock produces a lignocellulosic residue (e.g. distillers grain from grain, bagasse form sugar cane), the residue can be used directly as a lignocellulosic feedstock.

The integration with ethanol production from sugar/starch feedstock also opens the possibility for procuring raw material from the world market, which secures a safer raw material supply. It also opens the possibility to use whole crops as feedsstocks, which can substantially reduce the costs related to harvesting, storage and transportation.

Another advantageous option of the invented method is to integrate ethanol production with central power plants and take advantage of some of the low value thermal energy otherwise disposed of (sent to a condensing system). Additional cost reductions derive from lower investment costs by exploitation of the infrastructure of the power plant. If the residues (mainly lignin) are combusted at the power plant, further economical improvement can be achieved. Preferred embodiments of the method according to the invention produce a combustible residue of microparticles with a low content of KCl, which is well-suited for co-combustion with pulverized coal at central CHP plants with high electricity efficiency, which means that the value of the residues will be increased with around 30% compared with the value achieved when the residues are combusted in a small CHP designed for the energy demand of the biomass plant.

Example

Conversion of Wheat Straw

The conversion method of the invention has been tested on chopped wheat straw at pilot plant facilities comprising wet cleaning and chopping of straw, pre-soaking and pressurized pre-treatment in a reactor with two sections, with a first particle pump to load the soaked feedstock into the first section, and a second particle pump to transfer the feedstock into the second section, and a third particle pump to unload the fibre fraction from the second section. The particle pumps used in the pilot plant are described in WO 03/013714A1. This means, that three soaking-pressing operations could be conducted, using the particle pumps for the pressing process. In addition a washing step at ambient pressure was tested, by which the fibre fraction after soaking was pressed to around 40% dm with a screw press.

Evaluation of the effect of different pre-treatment conditions was based on data from downstream liquefaction, ethanol fermentation and distillation trials on pretreated straw.

Typical results from the conversion of pretreated straw are as follows.

Composition 1000 kg Wheat Straw:

| | |
|---|---|
| Moisture | 140 kg |
| Cellulose | 350 kg |
| Hemicellulose | 250 kg |
| Lignin | 150 kg |
| Ash | 50 kg |
| Others | 60 kg |

Process Conditions:
Presoaking: 80° C., 15 min
Pressurized Reactor:
1. section: 180° C., 10 min
2. section: 195° C., 3 min
3 Soaking Pressing Operations
Water:straw ratio: 5:1
Yields:

| | |
|---|---|
| Bioethanol | 150 kg |
| Solid biofuel (90% dm) (lignin and residual carbohydrates) | 250 kg |
| C5 Molasses (70% dm) Hemicellulose sugars, acetate, and others | 450 kg |

At these process conditions a maximum of 4% lignin or products deriving from lignin were contained in the C5 molasses (dry matter), corresponding to 12.6 kg or 8.4% of the lignin content of straw. This means that 91.6% of the lignin content of the straw is maintained in the fibre fraction.

Similar results could be achieved at process conditions where the first section of the pressurized reactor was operated at 180 C in 17 min. and the second section was by-passed.

The experience with wheat straw demonstrates that embodiments of the method of the invention can provide high conversion of the cellulose content of the straw to ethanol leaving around 90% of lignin as solid suspended particles which can be recovered by known means.

The process conditions (temperatures and retention times) of the invention can be adjusted to the economical optimum for each raw material.

End of Example

It should be understood that all features and achievements discussed above in relation to the invention of the first aspect of the invention and embodiments thereof apply to the invention of the second aspect of the invention discussed below and/or to embodiments thereof.

In a second aspect, the present invention provides an apparatus and a method for conversion of cellulosic material (CM) to ethanol and other products, the cellulosic material preferably comprising cellulose, as well as lignin, hemicellulose and alkali chlorides, and optionally sugars. The method of the second aspect of the present invention comprises continuous hydrothermal pre-treatment (HTP) without addition of acids or bases or other chemicals, which must be recovered, and subsequent enzymatic hydrolysis (EH), ethanol fermentation and recovery. The method comprises the steps of:

Adjusting the particle size of long-particle cellulosic material (CM), such as straw and stalks, by cutting and/or chopping before the cellulosic material (CM) is subjected to the hydrothermal pre-treatment (HTP). In a preferred particle size distribution, less than 5% of the particles are longer than about 20 cm, and less than 20% of the particles are between about 10 and about 20 cm. Cellulosic material (CM) including pieces of wood are preferably made into standard chips.

Maintaining the adjusted particle size, i.e. maintaining the particle structure during the hydrothermal pre-treatment and an initial part of the enzymatic hydrolysis (EH).

Performing the hydrothermal pre-treatment as an extraction with hot water, thereby producing a solid fraction (SF) containing more than 80% of said lignin comprised in the cellulosic material (CM), and a liquid fraction (LF) with a preferred content of hemicellulose sugars less than 80% of the original content in the CM, more preferred less than 70% of the original content in the CM, even more preferred less than 60% of the original content in the CM containing a majority of said alkali chlorides comprised in the cellulosic material (CM) and a majority of fermentation inhibitors produced by the hydrothermal pre-treatment (HTP).

Conveying the cellulosic material (CM) through at least one pressurised reactor defining a reactor pressure zone at an elevated pressure, the cellulosic material being heated to a temperature between 170 and 230° C. for effecting the hydrothermal pre-treatment. The temperature may be between 180 and 210° C., such as between 190 and 200° C.

Unloading the solid fraction (SF) from the reactor pressure zone to a first downstream pressure zone, which is at a lower pressure than the reactor pressure zone, preferably while collecting released steam without access for air. A preferred dry matter content is between 20-60% and more preferred 30-50% and most preferred 35-45%.

Unloading the liquid fraction (LF) from the pressurised reactor to a second pressure zone, which is at a lower pressure than the reactor pressure zone, preferably while collecting released steam without access for air.

The second aspect of the invention also provides an apparatus for conversion of cellulosic material (CM) to ethanol and other products, the cellulosic material preferably comprising cellulose, as well as lignin, hemicellulose and alkali chlorides, and optionally sugars, the apparatus conferring continuous hydrothermal pre-treatment (HTP) without addition of acids or bases and subsequent enzymatic hydrolysis (EH), ethanol fermentation and recovery, the apparatus comprising:

a cutting or chopping device for adjusting the particle size of long-particle cellulosic material (CM), such as straw and stalks, before the cellulosic material (CM) is subjected to the hydrothermal pre-treatment (HTP);

a hydrothermal pre-treatment device for effecting hydrothermal pre-treatment as an extraction with hot water, the hydrothermal pre-treatment device being adapted to maintain the adjusted particle size during the hydrothermal pre-treatment and to produce a solid fraction (SF) containing more than 80% of said lignin comprised in the cellulosic material (CM), and a liquid fraction (LF) containing a majority of said alkali chlorides comprised in the cellulosic material (CM), and a majority of fermentation inhibitors produced by the hydrothermal pre-treatment (HTP);

at least one pressurised reactor defining a reactor pressure zone at an elevated pressure, the cellulosic material being heated to a temperature between 170 and 230° C. for effecting the hydrothermal pre-treatment;

an unloading mechanism for unloading the solid fraction (SF) from the reactor pressure zone to a first downstream pressure zone, which is at a lower pressure than the reactor pressure zone, the unloading mechanism being preferably arranged to allow unloading while released steam is collected without access for air, and for unloading the liquid fraction (LF) from the pressurised reactor to a second pressure zone, which is at a lower pressure than the reactor pressure zone, preferably while collecting released steam without access for air.

In embodiments of the inventions of the first and second aspects of the invention, the second pressure zone may be an upstream pressure zone, such as a zone upstream of the reactor pressure zone. It may be downstream in relation to other zones, e.g. downstream of a cutting or chopping device for adjusting particle size of long-particle cellulosic material, and/or downstream of equipment for carrying out the hydrothermal pre-treatment.

Preferred embodiments of the method and apparatus of the second aspect of the present invention comprise particle size adjustment, hydrothermal pre-treatment with separation in a liquid and a solid fraction, different options for utilisation of the liquid fraction, enzymatic liquefaction and saccharification of the solid fraction, fermentation and recovery of ethanol, optional integration with ethanol production from sugar/starch feedstocks and optional integration with a combined heat and power (CHP) plant.

One effect of the embodiments of the present invention is improved economy of the conversion of lignocellulosic feedstock to ethanol. By introducing a method, wherein the particle structure of the feedstock is maintained, until the structure disappears during the enzymatic liquefaction (EL) step, and wherein the pre-treatment is conducted without addition of chemicals which have to be recovered, a number of interdependent cost reducing innovations can be implemented, and provide fuel ethanol from lignocellulose to a price similar to or lower than the price for ethanol from starch/sugar feedstocks.

The integration of ethanol production from lignocellulosic feedstocks with ethanol production from starch/sugar feedstocks is an advantageous option for the method of the invention because it can provide substantial reductions both in capital cost and cost of operation, especially in cases where it is difficult to collect enough lignocellulosic feedstock to produce about 100 000 t/y or more of fuel ethanol which is needed to take full advantage of the economy of scale. Furthermore, cost reductions can be achieved by using at least a part or a fraction of the liquid fraction (LF) from the pre-treatment to replace the water or part of it required in the mashing of starch/sugar feedstocks with high dry matter content. This is possible if the liquid fraction (LF) produced according to the invented method has a low or no content of inhibitors, which is usually the case. A significant part of the hemicellulose dissolved in the liquid fraction (LF) will be oligomers, and it is therefore possible to separate the liquid fraction (LF) into two fractions with ultra filtration. One fraction contains mainly pentose oligomers and has a high dry matter content, and the other fraction (the permeate) with low dry matter content contains mainly alkali chlorides and small organic molecules. This fraction is particularly suited for replacing water in the grain mashing (optionally cutting or chopping) process. During pre-treatment, the pH of the liquid fraction (LF) normally drops to around 3.5, which is preferably adjusted to the optimum for yeast by $NH_3$. The pentose fraction can be used as fermentation feedstock for ethanol production when relevant C5 sugar fermenting microorganisms are available. In the meantime it can be further concentrated and sold as feed for ruminants. Microorganisms in the ruminant can convert the pentose oligomers to short-chain fatty acids.

When the sugar/starch feedstock produces a lignocellulosic residue (e.g. distillers grain from grain, bagasse form sugar cane), the residue can be used directly as a lignocellulosic feedstock.

The integration with ethanol production from sugar/starch feedstock also opens the possibility for procuring raw material from the world market, which secures a safer raw material supply. It also opens the possibility to use whole crops as feedsstocks, which can substantially reduce the costs related to harvesting, storage and transportation.

Another advantageous option of the invented method is to integrate ethanol production with existing power plants and take advantage of some of the low value thermal energy otherwise disposed of (sent to a condensing system). Additional cost reductions derive from lower investment costs by exploitation of the infrastructure of the power plant. If the residues (mainly lignin) are combusted at the power plant, further economical improvement can be achieved. Preferred embodiments of the method according to the second aspect of the invention produce a combustible residue of microparticles with a low content of KCl, which is well-suited for co-combustion with pulverized coal at central CHP plants with high electricity efficiency, which means that the value of the residues will be increased with around 30% compared with the value achieved when the residues are combusted in a small CHP designed for the energy demand of the biomass plant.

Grinding of the lignocellulosic feedstocks before pre-treatment is one of the most electricity consuming process steps involved in the conversion cellulosic material (CM) of to ethanol. Most of the prior art methods use hammermills to produce small particles with a large surface area, but the effect of lignin as a strong thermoplastic glue makes it necessary at low temperatures to apply very strong mechanical forces to achieve the desired particle size.

Preferred embodiments of the present conversion method do not use grinding before pre-treatment at all, but maintain the particle structure throughout the pre-treatment in order to take advantage of the huge surface area provided by the cavities of cells and capillaries of the plant particles to create good reaction conditions for the hydrothermal pre-treatment (HTP) and for the following liquefaction step. At the high temperature of the hydrothermal pre-treatment (HTP), lignin is transformed to a liquid, loosing its properties as a glue, which means that only weak mechanical forces are required to open up the cell cavities to facilitate the access of the cellulytic enzymes to the interior surfaces of the particles.

Therefore, grinding can be replaced by a chopping process producing particles, where the major part have a length of less than about 10 cm and a minor part have a length of up to about 20 cm or about 30 cm.

It is an interesting effect of the apparatus and method of the present invention that chopped straw subjected to the hydrothermal pre-treatment (HTP) may have an energy content for ruminants more than twice the energy content of untreated straw, because of the improved access for digestive enzymes.

In respect of some types of dry feedstock such as straw, dust constitutes a problem, since it leads to poor working environment, risk for fires and dust explosions. These problems can be solved by wetting the feedstock, which will also facilitate the chopping process and reduce the specific energy consumption to a low level, which for straw is only about 25% of the demand for hammer milling. For straw and similar feedstocks it will often be advantageous to remove stones and other impurities and to perform the wetting in a wet stone trap.

The chopping of voluminous feedstock such as straw can be facilitated by compacting the feedstock before it enters into the chopping zone.

For forestry feedstocks, the chopping device may comprise or be replaced with a chipping device.

By feedstocks with small particles such as citrus, potato and sugar beet pulp, distillers grain and saw dust, no particle size reductions are needed, instead it can be an advantage to mix with a more fibrous feedstock.

The particle size adjustment is followed by the hydrothermal pre-treatment (HTP). The objective of the hydrothermal pre-treatment (HTP) is to make the cellulose accessible for enzymatic hydrolysis/attack.

The pre-treatment is based on extraction with water without addition of acids, bases or other chemicals which have to be recovered. This means that less dry matter is transferred from the feedstock to the liquid fraction (the extract) than by most other pre-treatment processes.

The transfer of hemicellulose sugars will normally be less than 60% and of lignin less than 20% of the original content of the feedstock. The hemicellulose will be hydrolysed but mostly to oligomers and soluble polymers, which can be further hydrolysed to fermentable sugars by enzymes.

Omitting addition of acids means low formation of fermentation inhibitors. Furthermore, the small amounts of inhibitors will be concentrated in the liquid fraction of the pre-treatment where a detoxification, if needed, can be conducted at low cost. If needed detoxification with $NH_3$ is preferred for the method according to the invention Omitting addition of acids, bases or other chemicals which have to be recovered also implies reduction of operational costs.

One first step of the hydrothermal pre-treatment (HTP) may comprise soaking, which may take place in the acetic acid containing liquid fraction from a subsequent step under ambient pressure and at temperatures up to 100° C. The objective of the soaking is to drive out air from the feedstock and to ensure that all of the feedstock is saturated with the liquid. A further objective is to utilise some of the energy of the liquid fraction to increase the temperature of the feedstock. Further objectives of the soaking step is to increase the dry matter content in the liquid fraction and to impregnate the feedstock with the organic acids generated by subsequent steps.

The next step may be a pressurized treatment at temperatures between 100° C. and about 230° C., carried out e.g. as a high-solids plug flow process.

In order to achieve the desired economical benefit, at least the pressurised part of the hydrothermal pre-treatment (HTP) should preferably take place with a high concentration of solids dry matter in the reactor. Thus, the reactor is preferably 100% filled, and for voluminous feedstocks compaction is an envisaged option. Continuous reactors with high solids dry matter content, based on a screw device, are often a cost effective solution, but in case of 100% filling, the transport function of the screw device may be insufficient. Embodiments of the reactor may thus include an intermeshing twin screw device or a single screw device with reciprocating axial movement.

The high concentration of solids dry matter in the reactor renders a flow through system as disclosed in U.S. Pat. No. 5,503,996 (Torget) in which flow through system fluid moves with respect to the solids unsuitable for most embodiments of the second aspect of the present invention. Instead, preferred embodiments of the second aspect of the present invention utilize a soaking/pressing system. In this context, soaking implies that the void volume of the solid is completely filled with liquid, whereas pressing implies that the major part of the liquid is removed again. The solids dry matter to liquid ratio during soaking should be as high as possible to produce high dry matter concentration in the liquid.

During transfer of the biomass from the soaking step to a subsequent pressurized treatment, the biomass is preferably dewatered in order to reduce the energy required to increase the temperature of the biomass to the level of the pressurized part of the hydrothermal pre-treatment (HTP). The temperature may be achieved by adding hot water and/or steam. The feedstock may be subjected to shearing forces at high temperature conditions in order to release the soft lignin from the cellulose. The shearing forces can be applied by different means e.g. by the transportation device in the reactor, by devices moved by the transportation device or by pressing during loading and unloading of the reactor. Shearing forces can also be applied by steam explosion, which primarily have the effect of blowing up the cells and capillaries. The means for applying shearing forces can be applied alone or as a combination of more than one means.

The solids dry matter concentration during soaking will typically be 10-20%, and after pressing 30-40% such that approximately 2.5-3.5 kg liquid per kg solids dry matter is added during soaking and removed again during pressing.

Each soaking and pressing step may transfer dry matter from the solids to the liquid fraction.

One objective of the hydrothermal pre-treatment (HTP) is to make the cellulose accessible for enzymatic hydrolysis/attack. It is not a particular objective to remove the hemicellulose and lignin from the solid fraction, but to neutralize their protection of the cellulose. It is presently believed that when lignin is melted in the presence of water, hydrophobic lignin will form micro-droplets which will solidify at lower temperatures and form micro-particles without any or very little cellulose protective effect. The lignin melting conditions of the hydrothermal pre-treatment (HTP) will hydrolyse the hemicellulose to a degree, where it will no longer protect the cellulose against enzymatic attack. It is also believed that the lignin melting conditions will eliminate crystallinity of the cellulose which is crucial to achieve efficient enzymatic hydrolysis. In order to improve the release of the melted lignin from the cellulose fibres, the feedstock is subjected to shearing forces. This will rub the lignin from the cellulose and facilitate the formation of free hydrophobic lignin droplets. The droplets seem to be coated by hydrophilic compounds mainly deriving from the partly hydrolysed hemicellulose. The resulting lignin microparticles have surprisingly no inhibiting effect on ethanol fermentation based on yeast or the C5 and C6 fermenting thermophiles under development by TMO Biotec Ltd, Guildford, UK.

One of the problems of industrial scale continuous, pre-treatment of voluminous feedstocks with high concentration of long particles is to transfer the feedstock into the pressurized reactor in a safe, efficient and reliable way. It is an advantage to load feedstocks into the reactor in portions with a sluice type loading device such as the particle pump described in WO 03/013714A1, wherein at any time at least one pressure lock secures pressure tight sealing between the pressurized reactor and the soaking vessel. This particle pump can remove liquid from soaked feedstock by pressing during loading and unloading, and unloading can be combined with steam explosion.

According to an embodiment of the second aspect of the present invention, the pressurized part of the hydrothermal pre-treatment (HTP) can be conducted at one or more sets of temperature/pressure conditions. Transfer of the feedstock from one pressure zone to another will normally be conducted by a sluice system with a pressing device. Additional pressing/soaking operations can be conducted within each pressure zone.

The pretreated feedstock can either be pressed, while it is still under high temperature conditions with lignin in the form of micro-droplets, or it can be pressed after it has been unloaded from the hydrothermal pre-treatment (HTP) reactor with lignin in the form of solid micro-particles.

One advantage of pressing before the feedstock is unloaded is that a higher dry matter content in the solid fraction (SF) can be achieved, possibly without extra drying. Another advantage by pressing under hot pressurized conditions is that the shearing forces generated during pressing will provide improved release of lignin droplets. One advantage of pressing at temperatures below 100° C. is that the cost is lower and that more lignin will remain in the solid fraction.

The depressurization of both the solid and the liquid fraction may be carried out in closed systems without access of air, in order to collect the released steam and to use the thermal energy of the steam for concentration purposes and the condensate as process water.

In order to achieve an efficient enzymatic liquefaction, it is desirable that as many enzymes as possible are placed on the surfaces of the accessible cellulose fibres contained in the particles of the pretreated solid fraction (SF). To achieve this, the warm pressed solid fraction (SF) is mixed with a colder enzyme preparation which may be sucked into the cavities of the particles. The steam trapped in the cavities condenses as it is cooled by the enzyme preparation and creates a vacuum pulling the enzyme preparation into the cavities. By adjusting the concentration of enzymes in the preparation, the desired amount of enzymes can be placed at the inner and outer surfaces of the particles, adhering to the cellulose fibres. By virtue of this adhesion, the dry matter content of the enzyme-loaded solid fraction (SF) can be increased by pressing, while preventing removal of enzymes to an unacceptable extent.

By adjusting the temperature and pH of the enzyme preparation before mixing with the warmer pretreated SF the optimal liquefaction conditions can be achieved.

As described by Tolan, enzyme preparations for hydrolysis of cellulose will normally contain three types of enzymes: endogluconase, cellobiohydrolase and beta-glucosidase. The first two hydrolyse the polymer cellulose to its soluble dimer cellobiose which is then hydrolysed to glucose by the third type. Product inhibition from cellobiose and glucose can be prevented or reduced by increasing the concentration of beta-glucosidase and use separate hydrolysation and fermentation. Another solution is to use the simultaneous saccharification and fermentation (SSF) process, wherein the cellobiose and the glucose are converted to ethanol by the fermenting organism. One embodiment of the present invention is based on a succesfull development of thermophilic ethanologenic microorganisms with the capacity to ferment both C5 and C6 sugars and compatible enzyme systems with high hemicellulase and cellulase activity at temperatures around 60° C. and at pH around 6. Of special interest for the present invention is thermophiles with the capacity to ferment not only monomers but also small oligomers such as cellobiose, maltose and raffinose simultaneously, which together with a compatible enzyme system will create the ideal simultaneous saccharification and fermentation process (SSF) to convert the pretreated biomass of the invention to ethanol. As an alternative, the method according to the invention may use an approach, in which a separate liquefaction step is introduced, providing optimal conditions for the activity of the enzymes followed by simultaneous saccharification and fermentation process (SSF) with the liquefied fraction as substrate and with optimal conditions for the fermentation organism, but suboptimal conditions for the enzymes.

During the liquefaction step catalysed for example by Tricoderma cellulase at pH around 5 and temperature around 50° C. the endogluconase may provide most of the depolymerisation because the activity of the cellobiohydrolase is swiftly inhibited by accumulated cellobiose and the beta-glucosidase is inhibited by accumulated glucose.

The liquefaction can be conducted by two principles, wet or solid state liquefaction.

By solid state liquefaction, the enzyme-loaded solid fraction (SF) is transferred into a mixer, which does not contain free liquid in the inlet area.

At solid state liquefaction on industrial scale, the microscopic movement of the enzymes from attack to attack on the cellulose may not always be provided by conventional stirring, because of the great power input required to overcome friction between the particles. Instead, technology used in the composting industry can be applied, such as composting drums, where the solid fraction (SF) loaded with enzymes is subjected to a number of lifts and falls during the transport through the cylindrical drum, which is rotating or stationary and equipped with a rotor with lifting devices.

By liquid state liquefaction, the incoming enzyme loaded particles of the solid fraction (SF) is submerged into the viscous liquid of liquefied material. Even though the mixture may be highly viscous, the mixing can be carried out by a variety of known mixing devices.

Some advantages of liquid state liquefaction are:
dry matter loading of the reactor can be high,
transmission of suitable forces to ensure that the enzymes move from attack to attack on the cellulose is facilitated by the liquid,
recycling of liquefied fraction with enzymes to inlet region is possible.

The liquefaction reactor according to the present invention can be based on an elongated cylindrical container with an inlet for the enzyme-loaded solid fraction (SF) at a top portion of one end of the container and an outlet for the liquefied fraction (LfF) at a bottom portion of another end of the container.

At the inlet, a perforated piston device may force the particles of the solid fraction (SF) towards the outlet, completely submerged in the liquefied fraction. At the outlet, a screening device may separate the residual particles (RP), consisting mainly of cellulose and lignin, from the liquefied fraction (LfF) consisting mainly of a solution of liquefied polysaccharides and lignin microparticles. During the passage through the reactor, the structure of most of the (SF) particles will gradually disappear, while residual particles (RP) may be sorted out, disintegrated and recycled to the inlet of the reactor.

The reactor can be stirred by appropriate conventional stirring devices, and additionally vibrations can be applied using oscillations from a few millimeters down to ultra sonic waves. After removal of the residual particles (RP) from the LfF, the micro-particles of lignin can be removed on a plate and frame filter providing a filter cake with a dry matter content as high as 70%, whereby low drying costs are achieved. This product usually has a low content of KCl and can therefore be combusted in combined heat and power plants with high electricity efficiency. The filtrate may be pumped to a feed tank, where temperature, pH and the content of nutrients may be adjusted to optimize the conditions of the subsequent simultaneous saccharification and fermentation process (SSF). If the simultaneous saccharification and fermentation process (SSF) is based on yeast, the temperature should be lowered to about 35° C. whereas the pH 5 can be maintained.

If the simultaneous saccharification and fermentation process (SSF) process is based on a C6 and C5 fermenting thermophile microorganism, such as TMO Biotec's thermophiles, the temperature may have to be increased to about 60° C. and the pH to about 6.

The simultaneous saccharification and fermentation process (SSF) disclosed herein can be carried out as a fed batch or a continuous process relying on equipment known per se.

Recovery of ethanol can be carried out by conventional distillation technology.

A preferred recovery technology for the present invention is to use a stripping technology, such as vacuum stripping, gas stripping or spray evaporation, by which the temperature of the broth can be kept close to the fermentation temperature during removal of the ethanol.

Thereby, thermal inactivation of enzymes and fermenting organisms is limited, and the enzymes and fermenting organisms can therefore be recycled and provide further cost reductions.

The lignin microparticles can be kept in the liquefied fraction during fermentation because no inhibitory effect is associated with the microparticles of macromolecular lignin. Simultaneous ethanol fermentation and recovery is an interesting cost reducing option for the method according to the invention wherein the ethanol will be removed before inhibition starts to slow down the rate of fermentation. The recovery of ethanol during fermentation may be conducted by gas stripping using the principle of spray-evaporation by which the ethanol can be removed from the broth without thermal inhibition of enzymes and microorganisms which can be recycled to the fermentor.

Figure 2:
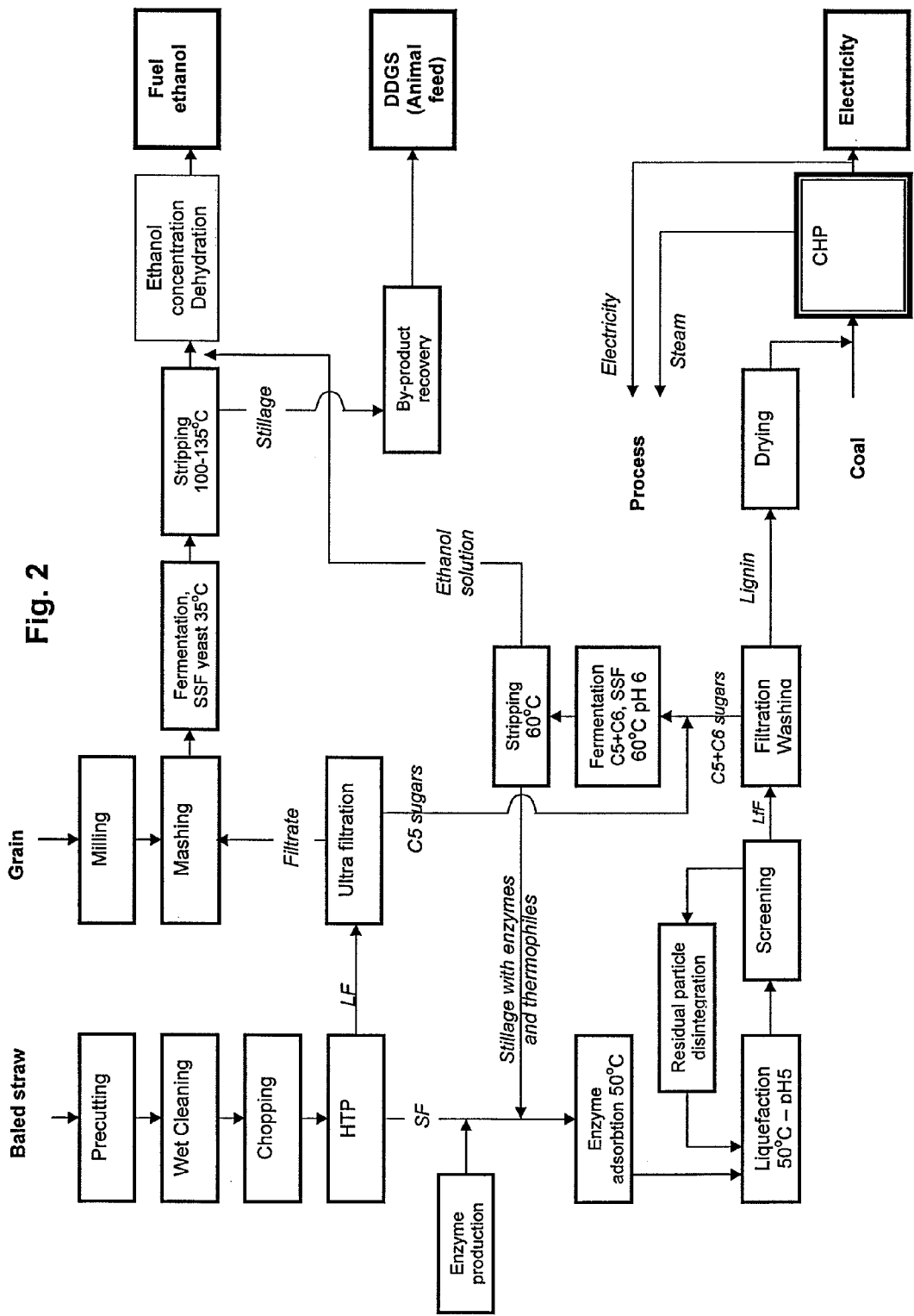
Figure 3:
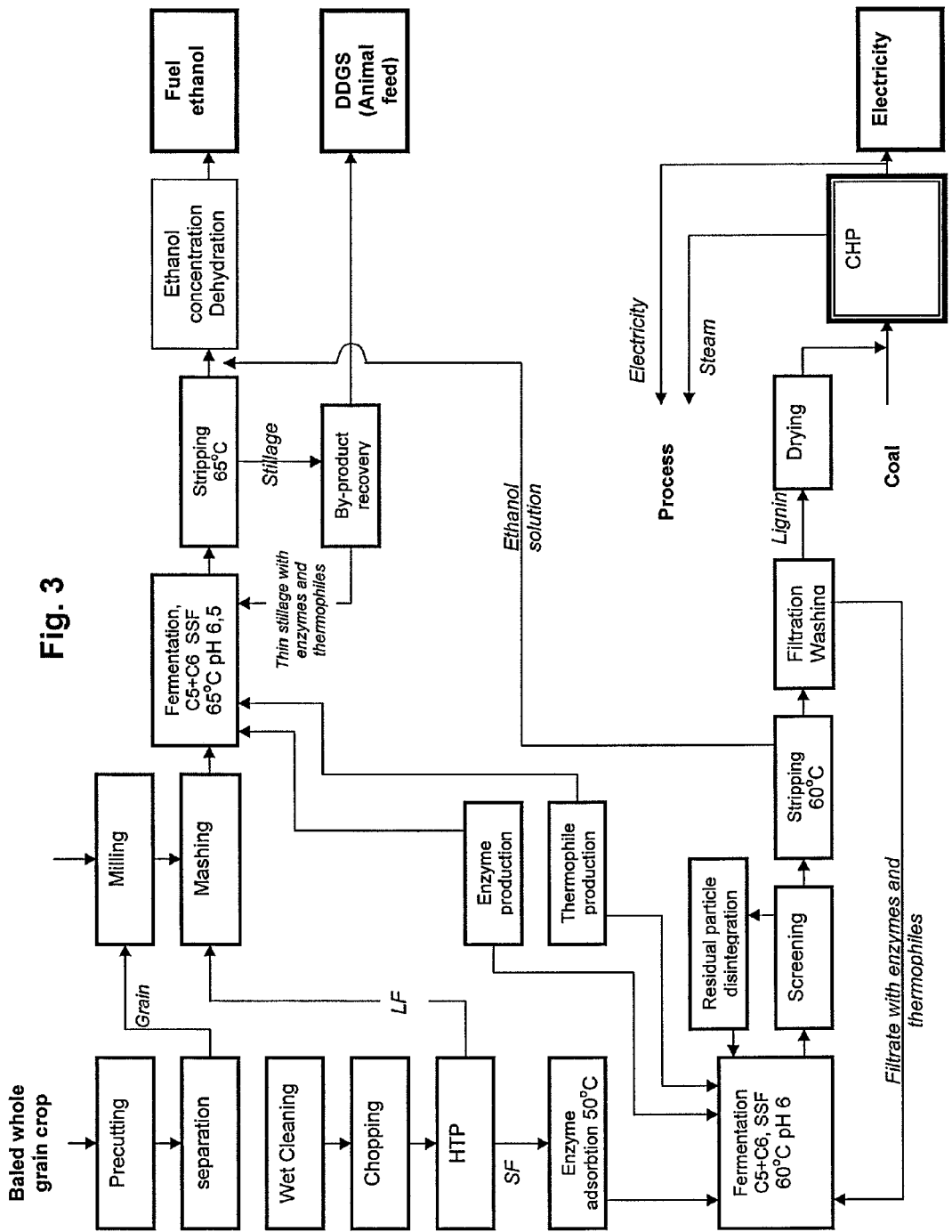

The flow diagrams in FIGS. 1-3 illustrate different examples of preferred embodiments of the present conversion method.

FIG. 1 shows conversion of baled straw and grain in a situation where the competitiveness of thermophilic C5 and C6 sugars fermentation is too low. Therefore, the C5 and C6 sugars released from the solid fraction (SF) of the straw are united with the C6 sugars from the grain and subjected to yeast fermentation. Only the C6 sugars are converted to ethanol. The C5 sugars increase the solubles dry matter of the stillage, and are together with the C5 sugars of the liquid fraction (LF) collected in the DDGS.

FIG. 2 illustrates an embodiment, in which the thermophilic fermentation can compete with yeast when C5 and C6 sugars are mixed, but not by pure C6 fermentation. Furthermore, compatible systems of thermophiles and enzymes are not ready for industrial use. Therefore, two separate fermentations are employed. The permeate from ultra filtration of the liquid fraction (LF) is used to replace water in the mashing of grain, as in the embodiment of FIG. 1.

The ethanol solution from the straw process is concentrated and dehydrated in the grain process.

FIG. 3 illustrates an embodiment involving C5 and C6 sugar fermenting thermophiles only. Because of the different enzyme systems needed for straw and grain, two separate simultaneous saccharification and fermentation processes (SSF) are provided. Simultaneous saccharification and fermentation processes (SSF) in respect of straw is conducted at a lower temperature and pH than the simultaneous saccharification and fermentation processes (SSF) in respect of grain in order to match the demand of the enzyme system. The liquid fraction is fed directly to the grain mashing process.

It should be understood that all features and achievements discussed above in relation to the invention of the second aspect of the invention and embodiments thereof apply to the invention of the first aspect of the invention discussed above and/or to embodiments thereof.

The invention claimed is:

1. A method for conversion of a cellulosic material, comprising an enzymatic liquefaction of said cellulosic material at high dry matter content, said method comprising the steps of:
   conveyance of cellulosic material through at least one pressurized hydrothermal pre-treatment reactor, followed by pressing to create a fibre fraction having dry matter content between 20-60% w/w and a liquid fraction;
   application of enzymes to the fibre fraction to create an enzyme-loaded fibre fraction; followed by
   mixing of the enzyme-loaded fibre fraction to provide liquefied material; followed by
   submersion of enzyme-loaded fibre fraction into the liquefied material obtained from mixing enzyme-loaded fibre fraction.

2. A method according to claim 1, wherein said cellulosic material is a lignocellulosic material.

3. A method according to claim 2, wherein said lignocellulosic material is selected from the group comprising: chopped straw, corn stover, chopped whole cereal, corn crops, bagasse and wood chips.

4. A method according to claim 1, wherein said hydrothermal pretreatment involves heating of said cellulosic material to a temperature of between 170° C. and 230° C.

5. A method according to claim 1, wherein said cellulosic material has been subjected to cutting, chopping, grinding or milling for particle size adjustment.

6. A method according to claim 1, wherein said cellulosic material has been soaked at ambient pressures and temperatures up to 100° C. prior to the pressurized part of the hydrothermal pretreatment.

7. A method according to claim 6, wherein said cellulosic material is dewatered prior to entering said hydrothermal pretreatment reactor.

8. A method according to claim 1, wherein said hydrothermal pretreatment takes place without addition of acids or bases or other chemicals, which must be recovered.

9. A method according to claim 1, wherein said enzyme is selected from the group comprising: endogluconase, cellobiohydrolase and beta-glucosidase.

10. A method according to claim 1, wherein said application of enzymes to said fibre fraction is performed by mixing relatively warm fibre fraction with relatively cold enzymes.

11. A method according to claim 10, wherein the dry matter content of the enzyme loaded fibre fraction is increased by pressing.

* * * * *